United States Patent
Batenchuk et al.

(10) Patent No.: US 12,175,738 B2
(45) Date of Patent: *Dec. 24, 2024

(54) SYSTEMS AND METHODS FOR USING IMAGE PROCESSING TO GENERATE INFERENCES OF BIOMARKER FOR IMMUNOTHERAPY

(71) Applicant: Verily Life Sciences LLC, South San Francisco, CA (US)

(72) Inventors: Cory Batenchuk, South San Francisco, CA (US); Huang-Wei Chang, Sunnyvale, CA (US); Peter Cimermancic, Mountain View, CA (US); Kimary Kulig, San Francisco, CA (US); Graziella Solinas, San Francisco, CA (US)

(73) Assignee: VERILY LIFE SCIENCES LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/191,170

(22) Filed: Mar. 28, 2023

(65) Prior Publication Data

US 2023/0245439 A1 Aug. 3, 2023

Related U.S. Application Data

(63) Continuation of application No. 16/601,220, filed on Oct. 14, 2019, now Pat. No. 11,629,384.

(Continued)

(51) Int. Cl.
*G06V 10/82* (2022.01)
*C12Q 1/6886* (2018.01)
(Continued)

(52) U.S. Cl.
CPC ............ *G06V 10/82* (2022.01); *C12Q 1/6886* (2013.01); *G06T 7/0012* (2013.01); *G06T 7/13* (2017.01);
(Continued)

(58) Field of Classification Search
CPC ......... G06T 7/337; G06T 7/0012; G06T 7/13; G06T 7/155; G06T 2207/20021;
(Continued)

(56) References Cited

U.S. PATENT DOCUMENTS

2016/0304969 A1* 10/2016 Ayers ................... C12Q 1/6886
2016/0314335 A1* 10/2016 Al-Kofahi ............... G06T 7/187
(Continued)

FOREIGN PATENT DOCUMENTS

WO WO-2014165422 A1 * 10/2014 ....... G01N 33/57415
WO 2016075096 A1 5/2016
(Continued)

OTHER PUBLICATIONS

"Artificial intelligence can determine lung cancertype: Tool also IDs genetic changes in each patient's tumor", NYU Langone Health / NYU School of Medicine, Sep. 17, 2018 (https://www.sciencedaily.com/releases/2018/09/18091711 1642.htm), 3 pages.

(Continued)

*Primary Examiner* — Nizar N Sivji
(74) *Attorney, Agent, or Firm* — Kilpatrick Townsend & Stockton LLP

(57) ABSTRACT

Methods and systems are disclosed for image process biological samples to infer biomarker values. An image of a biological sample can be accessed. The image can be segmented into a set of patches. Edge detection performed on each patch can be used to identify one or more biological features represented by the patch. An indication of the one or more features of each patch may be used to generate one (Continued)

or more image level metrics. A value of a biomarker may be inferred using the one or more image level metrics. The value of the biomarker can then be output.

**20 Claims, 7 Drawing Sheets
(4 of 7 Drawing Sheet(s) Filed in Color)**

Related U.S. Application Data

(60) Provisional application No. 62/775,129, filed on Dec. 4, 2018, provisional application No. 62/747,415, filed on Oct. 18, 2018.

(51) Int. Cl.
*G06T 7/00* (2017.01)
*G06T 7/13* (2017.01)
*G06T 7/155* (2017.01)
*G06V 10/44* (2022.01)
*G06V 10/56* (2022.01)
*G06V 10/75* (2022.01)
*G06V 20/69* (2022.01)

(52) U.S. Cl.
CPC .............. *G06T 7/155* (2017.01); *G06V 10/44* (2022.01); *G06V 10/454* (2022.01); *G06V 10/56* (2022.01); *G06V 10/758* (2022.01); *G06V 20/698* (2022.01)

(58) Field of Classification Search
CPC . G06T 2207/20084; G06T 2207/30061; G06T 2207/10056; G06T 2207/30024; G06T 2207/30096; G06V 20/69; G06V 20/695; G06V 10/82; G06V 10/454; G06V 10/758; G06V 10/44; G06V 10/56; G06V 20/698; C12Q 1/6886
See application file for complete search history.

(56) References Cited

U.S. PATENT DOCUMENTS

| | | | | |
|---|---|---|---|---|
| 2017/0091527 A1* | 3/2017 | Sarachan | ........... | G06V 10/7715 |
| 2017/0372117 A1* | 12/2017 | Bredno | ...................... | G06T 7/00 |
| 2018/0148790 A1* | 5/2018 | Ayers | ................... | G01N 33/543 |
| 2019/0392578 A1* | 12/2019 | Chukka | ................ | G06V 20/695 |
| 2019/0392580 A1* | 12/2019 | Kapil | ................... | G06V 20/695 |
| 2020/0123618 A1 | 4/2020 | Batenchuk et al. | | |
| 2020/0302603 A1* | 9/2020 | Barnes | .................... | G06T 7/162 |
| 2021/0222254 A1* | 7/2021 | Faruki | ................. | C12Q 1/6886 |

FOREIGN PATENT DOCUMENTS

| | | | | |
|---|---|---|---|---|
| WO | 2016160491 A1 | 10/2016 | | |
| WO | WO-2017051195 A1 * | 3/2017 | ........... | G06T 7/0012 |
| WO | WO-2017198790 A1 * | 11/2017 | ........... | G06T 7/0012 |
| WO | 2020081463 A1 | 4/2020 | | |

OTHER PUBLICATIONS

U.S. Appl. No. 16/601,220, "Non-Final Office Action", May 26, 2022, 14 pages.
U.S. Appl. No. 16/601,220, "Notice of Allowance", Dec. 14, 2022, 7 pages.
Ascierto et al., "Future Perspectives in Melanoma Research", Journal of Translational Medicine, vol. 14, No. 313, 2016, 25 pages.
Barrios et al., "Interactive Border Detection in Cellular Images Using a Kohonen Neural Network", WIT Transactions on Biomedicine and Health, vol. 3, 1996, 7 pages.
Caicedo et al., "Data-analysis strategies forimage-based cell profiling", Nature Methods vol. 14, pp. 849-863 (2017), 15 pages.
Koelzer et al., "Digital Image Analysis Improves Precision of Pd-L1 Scoring In Cutaneous Melanoma", Histopathology, vol. 73, No. 3, 2018, pp. 397-406.
Linguraru et al., "Tumor Burden Analysis on Computed Tomography by Automated Liver and Tumor Segmentation", IEEE Trans Med Imaging. 31(10), Oct. 2012, 30 pages.
Ljosa et al., "Introduction to the Quantitative Analysis of Two-Dimensional Fluorescence Microscopy Images for Cell-Based Screening", PLOS Computational Biology, vol. 5, No. 12, e1000603, 2009, 10 pages.
Masucci et al., "Validation of Biomarkers to Predict Response to Immunotherapy in Cancer: vol. I—Pre-Analytical and Analytical Validation", Journal for Immuno Therapy of Cancer, vol. 4, No. 76, 2016, 25 pages.
PCT/US2019/056140, "International Search Report and Written Opinion", Jan. 15, 2020, 13 pages.
Sade-Feldman et al., "Resistance to Checkpoint Blockade Therapy Through Inactivation of Antigen Presentation", Nature Communications, vol. 8, No. 1136, Oct. 2017, pp. 1-11.
Vivanti et al., "Automatic detection of new tumors and tumorburden evaluation in longitudinal liver CT scan studies", Int J Cars (2017) 12, Aug. 30, 2017, pp. 1945-1957.
European Application No. 19798771.2, "Office Action", Oct. 2, 2024, 6 pages.

* cited by examiner

SYSTEMS AND METHODS FOR USING IMAGE PROCESSING TO GENERATE INFERENCES OF BIOMARKER FOR IMMUNOTHERAPY

CROSS REFERENCE TO RELATED APPLICATIONS

This application is a continuation of U.S. patent application Ser. No. 16/601,220 filed Oct. 14, 2019, which claims the benefit of and priority to U.S. Provisional Application 62/775,129, filed Dec. 4, 2018, and U.S. Provisional Application No. 62/747,415, filed Oct. 18, 2018. Each of these applications is hereby incorporated by reference in their entireties for all purposes.

BACKGROUND

Immunotherapy is becoming increasingly utilized as a treatment approach for a variety of diseases, such as various cancers. It is predicted that 50% of all immunotherapy will be used to treat lung cancer by 2020, due to the high prevalence of the disease, in combination with the relatively high efficacy of immunotherapy as a treatment for lung cancer.

There are many different types of immunotherapies that may be effective in treating cancers. For example, "checkpoint inhibitors such as in programmed cell death protein 1 (PD-1) inhibitors (e.g., Pembrolizumab and Nivolumab), programmed cell death ligand 1 (PD-L1) inhibitors (e.g., Atezolizumab and Durvalumab), and CTLA-4 inhibitors (e.g., Ipilimumab) can re-activate T-cell recognition of tumor cells using different mechanisms of actions. Mechanisms can include blocking checkpoint inhibitors expressed by tumor cells or tumor stroma, which induce T-cell anergy, exhaustion and senescence. Once blocked, T-Cells can become reactivated and remove tumor cells through recognition of distinct tumor antigens (i.e., mutations).

To promote the safe and effective use of these agents, a number of diagnostics have emerged for the use of immunotherapy in lung cancer. Some of the diagnostics are companion diagnostics such that testing may be required to determine patient eligibility for a corresponding immunotherapy drug. One companion diagnostic is a PD-L1 immunohistochemistry assay, which measures PD-L1 protein expression on the surface of tumor cells. The result interpretation is based on the theory that a greater level of PD-L1 expression indicates greater dependence on this pathway for immune evasion and a greater probability of response to the PD-1/L1 checkpoint blockade. The second diagnostic assesses tumor mutational burden (TMB) through DNA sequencing of the tumor tissue. This concept is emerging for combination checkpoint therapies (e.g. Nivolumab+Ipilimumab), which go beyond the PD-L1 signaling axis. The result interpretation for this diagnostic is based on the theory that a larger tumor mutational burden indicates a greater probability that a patient has a neoantigen that will be recognized by a T-cell upon re-activation. The third diagnostic assesses an interferon gamma (IFNγ) gene expression signature also through DNA sequencing of the tumor tissue. A high IFNγ gene expression signature indicates a greater probability of response and survival to the PD-1/L1 checkpoint blockade versus a low IFNγ gene expression signature. PD-L1 can be upregulated through IFNγ signaling, thereby improving immunotherapeutic response.

Performing companion diagnostic testing is a time-intensive endeavor. Once obtained, the sample is transported to a lab where it will be tested with a batch of biopsy samples from a number of patients' tumors. Performing a PD-L1 immunohistochemistry assay can take two to seven days. Performing a TMB diagnostic can take up to three weeks which—on average, for patients with Stage-IV Non-Small Cell Lung Cancer (NSCLC)—represents 25-40% of patients' remaining life span when not treated. Further, the DNA sequencing frequently fails. There is insufficient material for the test 40% of the time, and the test fails quality control 40% of the time. Determining an optimal treatment plan in this instance is tricky, in that 55% of patients are TMB low or negative, and an assumption of either TMB test result would frequently be wrong and lead to sub-optimal treatment. Thus, the time from biopsy to a diagnostic test result may take up a significant portion of the patient's remaining life.

Thus, it would be advantageous to identify a fast and reliable technique for estimating a patient's PD-L1, TMB, and IFNγ status.

SUMMARY

In some embodiments, a computer-implemented method is provided. A microscopic image of at least part of a biological sample (e.g., a stained biological sample) is accessed. One or more portions of the microscopic image are detected that correspond to the stained biological sample. For each portion of the one or more portions of the microscopic image, a biological feature is identified. The biological feature is of a set of possible biological features that is represented by the portion. The detection of the biological feature includes detecting one or more edges within the portion based on differences in pixel intensities between adjacent pixels and identifying the biological feature based on the detected edges. One or more image level metrics are generated based on the biological features from the one or more portions of the microscopic image. A value of a biomarker represented in the stained biological sample is inferred based on the one or more image level metrics. The value of the biomarker can be associated with cancer (e.g., lung cancer or melanoma). The value of the biomarker is output.

The biomarker can include tumor mutational burden (TMB), programmed death ligand-1 (PDL1) or interferon gamma (IFNγ) gene signature. The biological feature can include tumor architecture (e.g. lepidic, papillary, mucinous, acinar, cribriform, solid, micropapillary, infiltrating lobular, medullary, mucinous, tubular, apocrine, solid/comedo, cribriform-comedo, comedonecrosis, serrated, signet ring cell, basaloid, clear cell, budding tumor foci, or single cell invasion), nuclear morphology (e.g. low nuclear grade, mid nuclear grade, high nuclear grade), endothelial vasculature, tumor associated fibroblasts, stromal fibroblasts, necrosis, mitotic figures, anthracotic pigment, debris, artefacts, keratin pearls, keratin sheaths, and/or other non-tumor structures. The one or more image level metrics can include a count of a feature, deriving spatial relationships within and between two or more biological features, and/or applying a kernel to identify feature topologies.

The method can further include one or more additional actions. The one or more additional actions can include assigning, based on the biomarker and for each identified biological feature, a weight to each aggregated biological feature dataset, wherein inferring the value of the biomarker represented in the stained biological sample is further based on the weight assigned to each aggregated biological feature dataset. The one or more additional actions can include generating a prediction of a clinical (including treatment-related) outcome of a patient based on the value of the biomarker. The one or more additional actions can include detecting a nuclear structure of one or more cells depicted in a portion of the microscopic image of the one or more portions of the microscopic image, where inferring the value of the biomarker can be further based on the nuclear structure of the one or more cells depicted in the microscopic image.

The one or more additional actions can include detecting a depiction of one or more immune cell sub-populations. The immune cell sub-populations can include one or more of small lymphocytes, macrophage, natural killer cells, neutrophils and/or eosinophils. The one or more additional actions can also include determining a quantity and/or a type associated with the one or more immune cell sub-populations. Inferring the value of the biomarker can be further based on the quantity and/or the type associated with one or more immune cell sub-populations.

In some embodiments, a computer-program product is provided that is tangibly embodied in a non-transitory machine-readable storage medium. The computer-program product includes instructions configured to cause one or more data processors to perform part or all of one or more methods disclosed herein.

In some embodiments, a system is provided that includes one or more data processors and a non-transitory computer readable storage medium. The non-transitory computer readable storage medium contains instructions which, when executed on the one or more data processors, cause the one or more data processors to perform part or all of one or more methods disclosed herein.

BRIEF DESCRIPTION OF THE DRAWINGS

Illustrative embodiments of the present invention are described in detail below with reference to the following drawing figures. The patent or application file contains at least one drawing executed in color. Copies of this patent or patent application publication with color drawing(s) will be provided by the Office upon request and payment of the necessary fee.

DESCRIPTION

Various techniques are provided for using image processing of images of biological samples to infer PD-L1 status, tumor mutational burden, or IFNγ gene expression signatures. In some instances, an image is parsed into a set of (overlapping or non-overlapping) patches. Each patch can be processed by an image processing system "Level 1" to classify/identify one or more features associated with the patch. Biological features (e.g., cell type, cellular feature, cellular architecture, morphology, and/or biomarker of interest) can be classified or identified. These features are then fed into a "Level 2" process that infers PD-L1 status, tumor mutational burden, or IFNγ gene expression signatures, and output.

Figure 1:
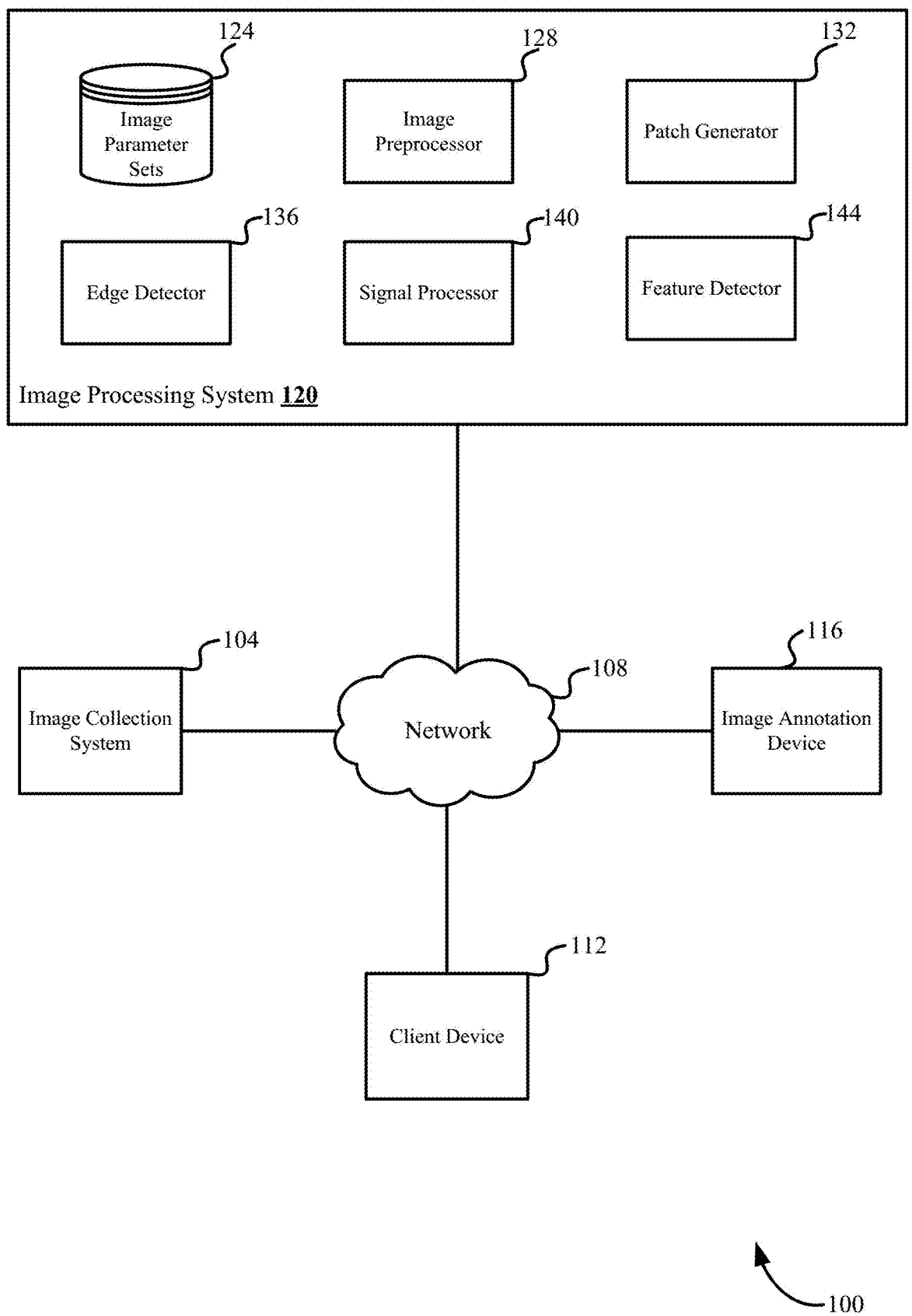
FIG. 1 depicts an exemplary system for using an image processing system to extract image parameters that define biological features used to infer PD-L1 status, tumor mutational burden, or IFNγ gene expression signatures using images of samples according to aspects of the present invention.

FIG. 1 depicts an interaction system 100 for using an image processing system to detect biological features to infer PD-L1 status, tumor mutational burden, or IFNγ gene expression signatures using images of samples according to aspects of the present invention. Interaction system 100 includes one or more image collection systems 104 to collect images to be used by an image processing system 120. The images may correspond to a set of biological samples. In some instances, the set of biological samples may be stained biological samples, which were stained with hematoxylin and eosin (H&E) or another stain.

In some instances, the images may be passed as input into an image processing system that can infer PD-L1 status, tumor mutational burden, and IFNγ gene expression signatures using a single image or multiple images of the same biological sample. For example, an image of a biological sample may be input into a Level 1 process that uses image processing techniques to identify biological features represented in one or more portions of the image. The output of the Level 1 process may be input into a Level 2 process that uses the identified biological features to infer PD-L1 status, tumor mutational burden, and IFNγ gene expression signatures. It will be appreciated that, in various instances, some or all of the Level 1 process and/or the Level 2 process may be performed by or in conjunction with one or more machine-learning models such as those described in U.S. Provisional Application 62/747,415 filed Oct. 18, 2018, which is hereby incorporated by reference in its entirety for all purposes.

The biological samples can include, but are not limited to, a sample collected via a biopsy (such as a core-needle biopsy), fine needle aspirate, surgical resection, or the like. A set of images may be processed by the image processing system. In some instances, each image of the set of images may correspond to different portions of the same biological sample or different biological samples.

Each of at least some (or all) of the images may correspond to a same biological sample type of biological structure, such that (for example) each of at least some (or all) of the images may correspond to a same anatomical structure (e.g. tumor type, location, biopsy method etc.).

Each of at least some (or all) of the set of images may be of a stained biological sample and/or can correspond to a same (or different) type of stain. In some instances, each of at least some (or all) of the set of images may be of a sample stained with (H&E).

Each of at least some (or all) of the set of images may include a magnified image with a magnification of (for example) at least 10×, about 10×, at least 40×, about 40×, at least 100×, about 100×, at least 400×, and/or about 400×. In some instances, each of the set of images has a same magnification. In some instances, at least some of the images of the set of images correspond to different magnifications.

Image collection system 104 can include (for example) a microscope (e.g., a light microscope) and/or a camera. In some instances, the camera is integrated within the microscope. The microscope can include a stage on which the portion of the sample (e.g., a slice mounted onto a slide) is placed, one or more lenses (e.g., one or more objective lenses and/or an eyepiece lens), one or more focuses, and/or a light source. The camera may be positioned such that a lens of the camera is adjacent to the eyepiece lens. In some instances, a lens of the camera is included within image collection system 104 in lieu of an eyepiece lens of a microscope. The camera can include one or more lenses, one or more focuses, one or more shutters, and/or a light source (e.g, a flash).

Image collection system 104 can be configured such that each portion of a sample (e.g., slide) is manually loaded onto a stage prior to imaging and/or such that a set of portions of one or more samples (e.g., a set of slides) are automatically and sequentially loaded onto a stage. In some instances, image collection system 104 includes a different surface instead of a stage, such as a rotating belt, on which samples can be placed. The image may be of an immunohistochemistry (IHC) slide, spatial transcriptomics, virtual stain, and/or a multiplexed immunofluorescence (mIF) slide. An mIF may be advantageous in that an IHC reporter (e.g., DAB) may not interfere with tar present in lung tissue of smoker subjects and/or mIE images can support a multiplexed approach by which multiple labels can be obtained on a single tissue slide (which can support multi-class classification and superior model performance).

Each image collected by image collection system 104 can include a digital image. Image collection system 104 can transmit one or more images (e.g., individually or in batch mode) over a network 108 to one or more other devices. Network 108 can include (for example) the Internet, a local area network, a wide area network or a short-range network. Network 108 can include a wireless network or a wired network (e.g. microscope connected to a computer). The digital image(s) can be transmitted in response to receiving a request for the image(s) (e.g., and verifying that the requesting entity is authorized to receive the image(s)) and/or can be pushed to a destination device (e.g., at routine intervals, upon collecting the image(s), upon detecting satisfaction of a transmission rule, etc.).

Image annotation device 116 can include one or more devices (e.g., a computer, tablet, smart phone, server, etc.) associated with an entity that assesses and annotates images. Image annotation device 116 can be configured to (for example) display (e.g., via a display or screen) the image, receive annotation and/or assessment input, map the annotation and/or assessment input to corresponding portion(s) of the image, store a representation of the annotation and/or assessment input (e.g., in correspondence with the portion(s) of the image) and/or output (e.g., present and/or transmit) the same or different representation of the annotations and/or assessment input. For example, the annotation and/or assessment input can include append an image with data such as, but not limited, characteristic from the patient from which the biological sample originated, characteristics of the image (e.g., number of pixels, origin, type of camera used, zoom used, type of microscope, etc.), or characteristics of related already processed images (e.g., in the case of multiple images of the same biological sample or of a different biological sample from the same patient or source). In some instances, image annotation device 116 may be embedded into the image collection system 104 (e.g., annotations being metadata attached to each image at the time of collection), client device 112, or image processing system 120.

In some instances, image annotation device 116 can transform detected annotated biological features as input annotation data (e.g., that indicate which pixel(s) of the image correspond to particular annotation characteristics). For example, image annotation device 116 associates a patient's smoking history with particular pixels in the image that depict possible smoking damage or staining. The association may be used by feature detector 144 in determining a value of the tumor mutational burden, PDL1 expression or IFNγ gene signature.

Image processing system 120 can include image parameter sets 124 that stores image properties, annotations, and/or metadata that is associated with the image being processed. Image parameters can include average pixel intensity, average color (e.g., RGB color values), resolution, and/or the like. In some instances, image parameter sets can additionally store image parameter sets (and the processed images) of one or more previous images that have been processed by image processing system 120. Each component 128-144 may execute one or more image processing techniques that produce one or more outputs (e.g., detected edges, modified or transformed versions of the image, identified biological structures or biological features, and/or the like) that may be stored in the image parameter sets 124 in association with the image being processed. Each component 128-144 may load the outputs generated from other components as part of further processing the image.

Image processing system 120 can include an image preprocessor 128 that modifies and/or transforms images into a form that improves the one or more image processing processes applied to the image. The preprocessing can include (for example) stain normalization, intensity normalization, color normalization (e.g., RGB values of pixels), affine transformations, and/or one or more image enhancements (e.g., blurring, sharpening, increasing or decreasing a resolution, and/or data perturbation). Properties of the image as a result of preprocessing can be detected and stored (in image parameter sets 124 or appended to the image via annotations or metadata). For example, properties of an image can be detected using a scale-invariant feature transform, pattern analysis, signal processing (e.g., coherence, Fourier based filtering, affine transformation, etc.) analysis, color and/or intensity analysis of pixels, and/or a transfer-learning model. In some instances, segmentation can be performed, such that individual pixels and/or detected figures can be associated with a particular structure such as, but not limited to, the biological sample, the slide and/or microscope staging, biological features, and/or the like.

Image preprocessor 128 can align multiple image (e.g., of different views of the same biological sample) to each other and scaling one or both of the images, such that they have a same scale. Stain normalization, for example, modifies the image properties of an images of biological samples stained according to different stain compositions or techniques (e.g., H&E, virtual staining, fluorescent, etc.) in which each stain compositions or technique may correspond to images with different variations in pixel color (e.g., in the red, green, blue color space) or intensities. Stain normalizing the image(s) can include (for example) normalizing pixel intensity values and/or one or more RGB values using a target statistic. The target statistic can be calculated using the pixel intensity one or more images (e.g., the mean, median, and/or mode of a set of images corresponding to different stain compositions and/or techniques). For example, an image of a sample stained with H&E stain may be normalized such that a mean, median, maximum, or mode intensity matches a mean, median, maximum or mode intensity of another image of the sample stained with an immunohistochemistry stain. As another example, an image of a sample stained with an immunohistochemistry stain may be normalized such that a spread, range or standard deviation of each of RGB values matches a corresponding statistic of another image of the sample stained with H&E stain.

In some instances, preprocessing techniques can convolve a kernel with an image to modify one or more pixels of the image. The kernel, as applied to the image, modifies the values of a pixel (e.g., color and/or intensity) based on the values of the pixel's neighbors and the values of the kernel. In some instances, only the values of the pixels immediate neighbors (e.g., the eight pixels that surround the pixel) may be used. In other instances, values of pixels that are further away from the pixel may be used to modify the value of the pixel. Different kernels may be convolved with different portions of the image. For example, the image processing system may convolve a first kernel with the entire image to normalize the image. The image processing system may convolve a second kernel and a third kernel with overlapping or non-overlapping portions of the image to blur and sharpen (respectively).

Image processing system 120 can include a patch generator 132 that generates a set of patches using an image. A patch can include a contiguous block of pixels from the image. Image processing system 120 may display individual patches, receive annotation-indicative inputs for specific patches and map annotation-indicative inputs to portions of particular patches. The set of patches may be non-overlapping with each other or partly overlapping with each other. In some instances, all patches within the set of patches have a same resolution and/or are a same size. In other instances, at least some of the set of patches have different resolutions and/or are of different sizes relative to each other. Adjusting a resolution from a resolution of a full image can include (for example) sampling pixels (e.g., so as to use RGB values associated with a pixel at a predefined relative position within a pixel block) and/or interpolating pixel values based on a set of adjacent pixels. In some instances, patch generator 132 generates patches in accordance with one or more predefined rules, such as a rule that identifies a size of each patch (e.g., in terms of absolute dimensions and/or pixel dimensions) and/or a degree of overlap between adjacent patches.

Due to the high resolution of the image, each patch itself includes a high degree of image detail, as illustrated in the three magnified exemplary patches. For example, an original image may include at least 1 million, at least 10 million, at least 100 million, at least 1 billion and/or at least 10 billion pixels. Individual patches may include at least 1,000, at least 10,000, at least 30,000 and/or at least 100,000 pixels. Patches can be generated such that at least 1,000, at least 10,000, at least 100,000, at least 250,000 and/or any number of patches (selected by a user and/or previous image processing information) are generated for an image.

Image processing system 120 can include an edge detector 136 that identifies edges depicted in an image. Edge detection can include one or more processing techniques that analyze contrasts across adjacent pixels or sets of pixels.

Edge detection may include a filtering technique in which one or more filters can be applied to the image and/or a patch. Filters may modify the image and/or patch by, blurring, sharpening, transforming (e.g., one or more affine transformations), and/or the like. Filters may reduce image noise by, for example, removing image artifacts and/or other portions of the image that do not correspond to the biological sample. Different filters may be applied to different portions of the image. For example, one patch may be filtered to sharpen the patch and another patch may be filtered by an affine transformation filter. A different number of filters may be applied to different patches. For example, some patches may be filtered by just an affine transformation while other patches may be filtered by an affine transformation and a Gaussian filter. Any number of different filters may be applied to the image and/or each patch.

Edge detection may include a technique that identifies pixel intensity gradients across adjacent pixels. For edge detection, large variations in the intensity between adjacent pixels can be indicative of the presence of an edge. For example, a first pixel with a high intensity value next to pixels with a low intensity values can provide an indication that the first pixel is part of an edge. In some instances, pixels that are not part of edges may be suppressed (e.g., set to a predetermined red/green/blue value, such as black, where red=0, blue=0, and green=0, or any predetermined red/green/blue value). An edge detection operator such a Roberts cross operator, a Prewitt operator, a Sobel operator, and/or the like may be used as part of the identification of the pixel intensity gradients process.

Edge detection may include a non-maximum suppression technique that suppresses pixels that do not correspond strongly to an edge. The non-maximum suppression process assigns an edge strength value to each pixel identified using the pixel intensity gradient as being part of an edge. For each pixel identified as being part of edge, the pixel's edge strength value can be compared to the edge strength value of the pixel's s eight surrounding pixels. If the pixel has a higher edge strength value than the edge strength value of the surrounding pixels (e.g., local maxima), then the surrounding pixels are suppressed. Non-maximum suppression may be repeated for each pixel in the entire image for the pixels in each patch of the set of patches, or the pixels in a particular one or more patches.

Edge detection may include a double threshold process that removes noise and/or spurious edge pixels that carried through application of previous image processing techniques applied herein. Two thresholds of pixel intensities may be defined, one high and one low. The thresholds may be used to assign an intensity property to each pixel as being strong or weak. Pixels that include an intensity value higher than the high threshold can be assigned a strong intensity property, where pixels that include an intensity value that is between the high threshold and the low threshold can be assigned a weak intensity property. Pixels that include an intensity value below the low threshold can be suppressed (e.g., in the same manner as described above).

Edge detection may include a hysteresis technique that removes pixels with a weak intensity property (that is weak due to noise, color variation, etc.). For example, a local statistical analysis (e.g., a connected-component analysis, etc.) may be performed for each pixel with a weak intensity property. Pixels with a weak intensity property that are not surrounded by a pixel that includes a strong intensity property may be suppressed. The remaining pixels (e.g., the un-suppressed pixels) after the hysteresis process include only those pixels that are part of edges. Although the above five processing processes were described in a particular order, each process may be executed any number of times (e.g., repeated), and/or executed in any order without departing from the spirit or the scope of the present disclosure. In some instances, only a subset of the five processes need be performed on the image. For example, image processing may perform identification of the pixel intensity gradients process without first performing a filtering process. In some instances, images may be received partially processed (e.g., one or more of the processes above having already been performed). In those instances, one or more additional processes may be performed to complete the image processing.

Image processing system 120 can include a signal processor 140. Signal processor 140 can be used to represent each pixel as a discrete collection of data points (e.g., similar to a radio frequency signal). The image may be transformed into a frequency domain (e.g., using a Fourier transform or the like) to represent the frequency in which a particular pixel characteristic exists in the image (e.g., pixel intensities, RGB values, pixels corresponding to particular biological features or structures, and/or the like). In the frequency domain, one or more filters (such as, but not limited to, Butterworth filters, band pass, and/or the like) may be applied to the image (e.g., during preprocessing, edge detection, or after) to suppress or alter particular frequencies. Suppressing particular frequencies can reduce noise, eliminate image artifacts, suppress non-edge pixels, eliminate pixels of particular colors or color gradients, normalize color gradients, and/or the like. A high-pass filter may reveal edges in an image (e.g., sharp contrasts of color and/or intensity between adjacent pixels) while a low-pass filer may blend edges (e.g., blur). Image padding may be performed prior to signal processing to improve the signal processing techniques. In some instances, different portions and/or patches of the image may be processed differently with some being processed with a high-pass filter and others with a low-pass filter. In some instances, the thresholds (e.g., the cutoff frequency for the high or low-pass filters) may be modified for different portions of the image (e.g., based on image processing one or more previous images, machine-learning, and/or the like).

Signal processor 140 may also determine other properties of the image such as coherence (e.g., used in edge detection, segmentation, pattern analysis, etc.), which identifies the relation between pixels. The relation between pixels can be used to further refine edge detection and/or to identify the structural properties of what is depicted within the image. For example, coherence can be used to identify portions of the image that are related (e.g., parts of a cell) from parts of the image that are not (e.g., a cell and part of the microscope staging captured in the image). The processes executed by the signal processor may be used to apply one or more of the image processing processes described above in connection with the image preprocessor 128 and edge detector 136. In some instances, signal processor 140 may apply one or more additional image processing techniques to the image after edge detection is performed.

Image processing system 120 can include a feature detector 144 that identifies and tags each patch as depicting one or more biological features. The feature detector may use detected edges, colors (e.g., RGB value of a pixel, block of pixels or area defined by one or more edges), intensities (e.g., of a pixel, block of pixels or area defined by one or more edges), and/or shapes (e.g., defined by detected edges, one or more pixels, etc.) to perform segmentation, pattern analysis, object recognition, and/or the like, as input into, convolutional neural network, a machine-learning model, and/or the like to identify the one or more biological feature shown by a patch (and/or the image). For example, feature detector 144 may indicate detected edges as corresponding to cell walls and the thickness of the edge as corresponding to the thickness of the cell wall. The thickness of the cell wall may inform the identification of the biological feature. Other characteristics detected by feature detector 144 and used to identify a biological feature include cell shape (e.g. circular), cell size, cell opacity, nuclear size, nuclear shape, cell wall thickness, location of the cell relative to other cells and/or tissue, cellular content of the region and/or the like.

Feature detector 144 may use the original image and/or just the processed image to detect one or more biological features that are shown by the image. Feature detector may use segmentation, convolutional neural network, object recognition, pattern analysis, machine-learning, a pathologist, and/or the like to detect the one or more biological features. Each patch can be analyzed by the feature detector to determine the one or more biological features shown in the patch. An identification of the one or more biological features depicted by a patch may be assigned (e.g., through a label, a data structure, annotation, metadata, image parameter and/or the like) to the patch.

In some instances, image processing system 120 processes an image to generate one or more feature maps. A feature map can be data structure that includes an indication of the one or more biological features assigned to each patch of the image. In some instances, the feature map can be rendered to depict the biological features tagged in each patch using, for example, text, color, animation, and/or the like based on the tagged one or more biological features.

The one or more biological features tagged in each patch may be used to generate one or more image level metrics. Feature detector 144 may identify the percentage of the image including each biological feature, density of each biological feature, a count of each biological feature in the image, proximity of a biological feature to another biological feature, spatial orientation of a biological feature, and/or the like. For example, a higher percentage of micropapillary features in the image may correspond to a higher tumor mutational burden. The image level metrics may be used to identify or include other characteristic of the image such as, but not limited to the source of the biological sample (e.g., site of biopsy).

A value corresponding to a biomarker (e.g., PD-L1 status, tumor mutational burden, or IFNγ gene expression signatures) can be generated based on the one or more image level metrics and/or the biological features identified in each patch. In some instances, one or more other characteristics associated with, but not necessarily shown by, the image such as, but not limited to, a smoking history, medical history, gender, or age of the patient from which the biological sample depicted in the image originated may also be used in inferring the value of the biomarker.

Tumor mutational burden can represent or indicate a quantity of distinct (i.e., unique) mutations found within a tumor. Tumor mutational burden can be experimentally quantified using DNA sequencing to evaluate the number of mutations across the entire exome of the tumor (whole exome sequencing), the entire genome of the tumor (whole genome sequencing) and/or across a specific panel of genes (e.g., those within Foundation One, Caris Molecular Intelligence, or MSK-Impact). Currently, tumor mutational burden refers to somatic mutations-specifically single nucleotide polymorphisms, but may change overtime to include structural variants (e.g. indels and copy number variations) as well. As such, tumor mutational burden can be described as a continuous variable (e.g. total number of mutations per genome, total number of gene mutations per genome, total number of gene mutations per exome, mutations per megabase pair, total mutations per gene sequencing panel, or total number of mutations inferred from panel sequencing results) or as a categorical variable (e.g. low, medium, or high). The tumor mutational burden can include an integer (e.g., to indicate a count of mutations) or a floating point number (e.g., to indicate a fraction of a total number of mutations that are inferred to be present in the imaged sample). A tumor mutational burden can include and/or be equivalent to a tumor mutation count, tumor mutation load, and/or tumor mutation status.

PD-L1 protein expression can represent or indicate a level of expression of corresponding PD-1 receptor. PD-L1, upon binding to the PD-1 receptor, may cause a transmission of an inhibitory signal that reduces antigen-specific T-cells and apoptosis in regulatory T-cells. The inhibitory effect of PD-L1 may enable cancers with an upregulation of PD-L1 to evade a host's immune system. A high tumpr expression of PD-L1 may indicate a greater probability of an immune response to the PD-1/L1 checkpoint blockade. PD-L1 protein expression can be quantified using immunohistochemisty (IHC) to evaluate expression at the protein level and/or quantified using polymerase chain reaction (PCR) or in-situ hybridization (ISH) to evaluate expression at the RNA level. PD-L1 expression may be quantified at the tissue level, or in specific compartments such as tumor cells, tumor immune infiltrate, or any combination thereof.

The IFNγ gene expression signature can represent or indicate a quantity of mRNA expression evaluating two or more of the following loci: IFNγ, STAT1, CD274, CCR5, CD8A, CCL5, PTPRC, CCL5, TBX21, CXCL9, CXCL10, CXCL11, CXCL13, IDO1, PRF1, GZMA, CD74, CCR5, CD2, IL2RB, CD3D, CD4, CXCR6, CD27, PRF1, GZMB, LAG3 and MHCII HLA-DRA. The IFNγ is a cytokine critical for adaptive immunity against viral, bacterial, and protozoal infections. In cancers, IFNγ has been shown to cause anti-proliferation (e.g., growth inhibition of tumors) and cell death (e.g., through apoptosis or autophagy). Methods used to evaluate gene expression of the above loci may be achieved through ISH, PCR, microarrays, RNA sequencing and/or barcode-based methods (e.g. Nanostring).

Image processing system 120 can transmit one or more results (e.g., the image, the data obtained through image processing of the image, the processed image, the value of the biomarker, and/or the like) to client device 112, which can present at least one of the one or more results. In some instances, client device 112 can present an original image along with the feature map. In some instances, the feature map may be rendered (e.g., via graphical user interface) on client device 112 to provide a user of the client device 112 a visual representation of the processed image.

Figure 2:
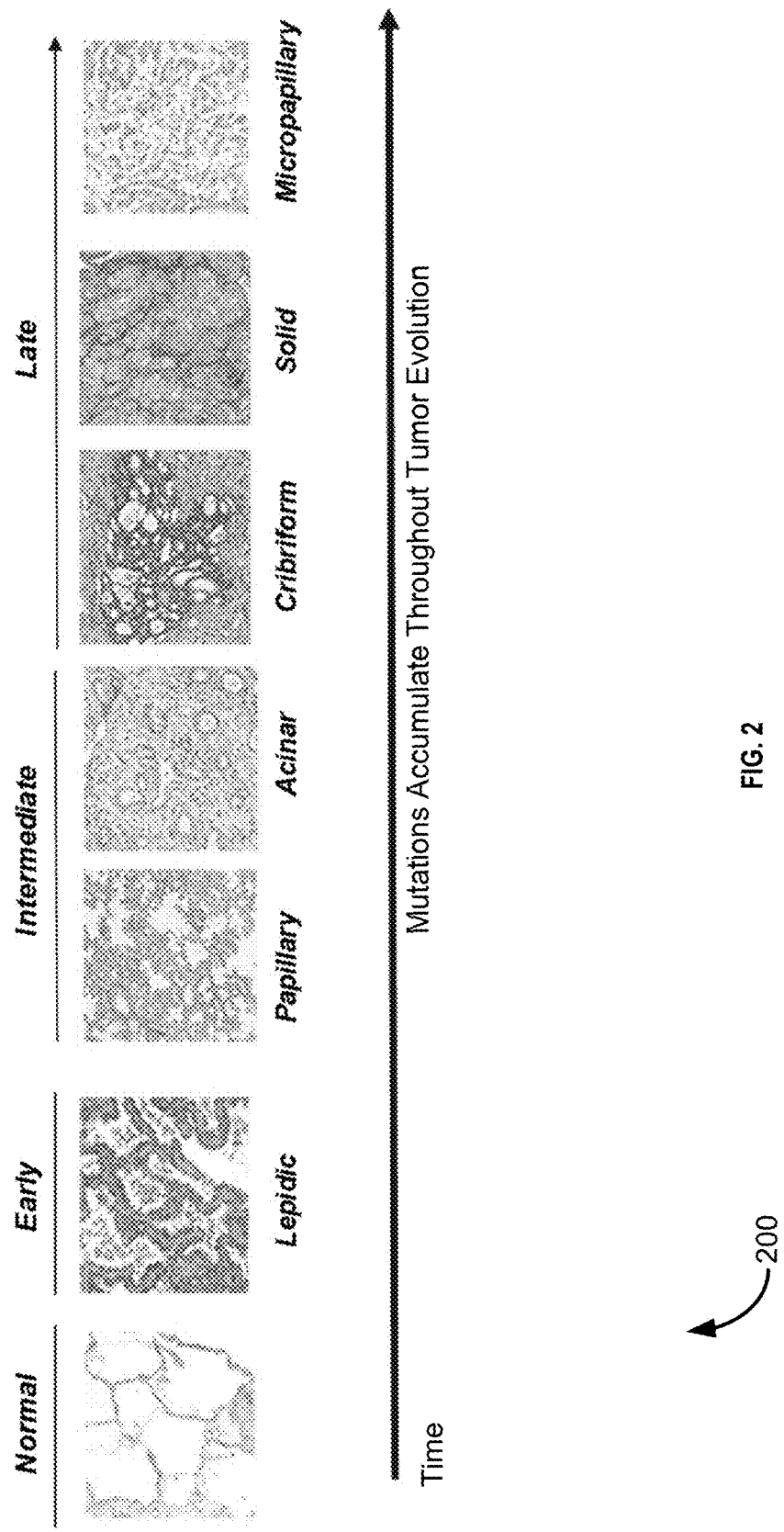
FIG. 2 illustrates exemplary biological features in lung adenocarcinoma that can be used to infer PD-L1 status, tumor mutational burden, or IFNγ gene expression signatures according to aspects of the present invention.

FIG. 2 illustrates exemplary biological features 200 that can be used to infer PD-L1 status, tumor mutational burden, or IFNγ gene expression signatures according to aspects of the present invention. Image processing may be performed on the image and/or on one or more patches of the image to identify a particular biological feature depicted in the image and/or each patch. In some instances, the one or more biological features include a feature of, or a categorization of, tissue such as, for example, mitotic figure, lymphocyte, macrophage, tumor cell, normal tissue, a specific tumor architecture (e.g. lepidic, papillary, mucinous, acinar, cribriform, solid, micropapillary, for adenocarcinoma lung cancer), nuclear morphology (e.g. low nuclear grade, mid nuclear grade, high nuclear grade, mitotic figures), or non tumor structures (e.g. endothelial vasculature, tumor associated fibroblasts, stromal fibroblasts, necrosis, anthracotic pigment, debris, artefacts, keratin pearls, keratin sheaths, and/or other non-tumor structures). While a patch may depict a biological feature, other patches may depict one or more other biological features. Thus, multiple different biological features may be identified as being shown in a single image (e.g., both papillary tissue and cribriform tissue, etc.). In some instances, a biological feature may also include the presence of other detectable aspects of a tumor or non-tumor tissue as described above (e.g. papillary tumor cell with mitotic figure present).

As tumor evolution progresses, tumors acquire more somatic mutations, and with the mutations, more neoantigens (e.g., antigen load) that can be recognized by the immune system. Identifying a biological feature depicted by a portion of the image and/or each patch can be used to infer the evolutionary progress of a tumor and thus a biomarker, such as, the tumor mutational burden (e.g., an indication of the number of mutations carried by tumor cells depicted in the image). In some instances, the image processing techniques may tag multiple discrete (overlapping or non-overlapping) portions of the image as depicting one biological features. In other instances, such as when image patching is performed, each patch may be tagged according to the biological feature depicted by the patch. In some instances, a statistical analysis (e.g., counting and/or regression analysis) can be applied to the classified portions of the image can be used to infer the tumor mutational burden. For example, the spatial relationship of each detected biological feature, application of a kernel to identify feature topology, percentage of each biological feature detected in the image, statistical sampling, density of each detected biological feature, proximity of a biological feature to another biological feature, spatial orientation of a biological feature, and/or like can be used to identify the PD-L1 status, tumor mutational burden, or IFNγ gene expression signatures from depiction of the tumor in an image.

Figure 3:
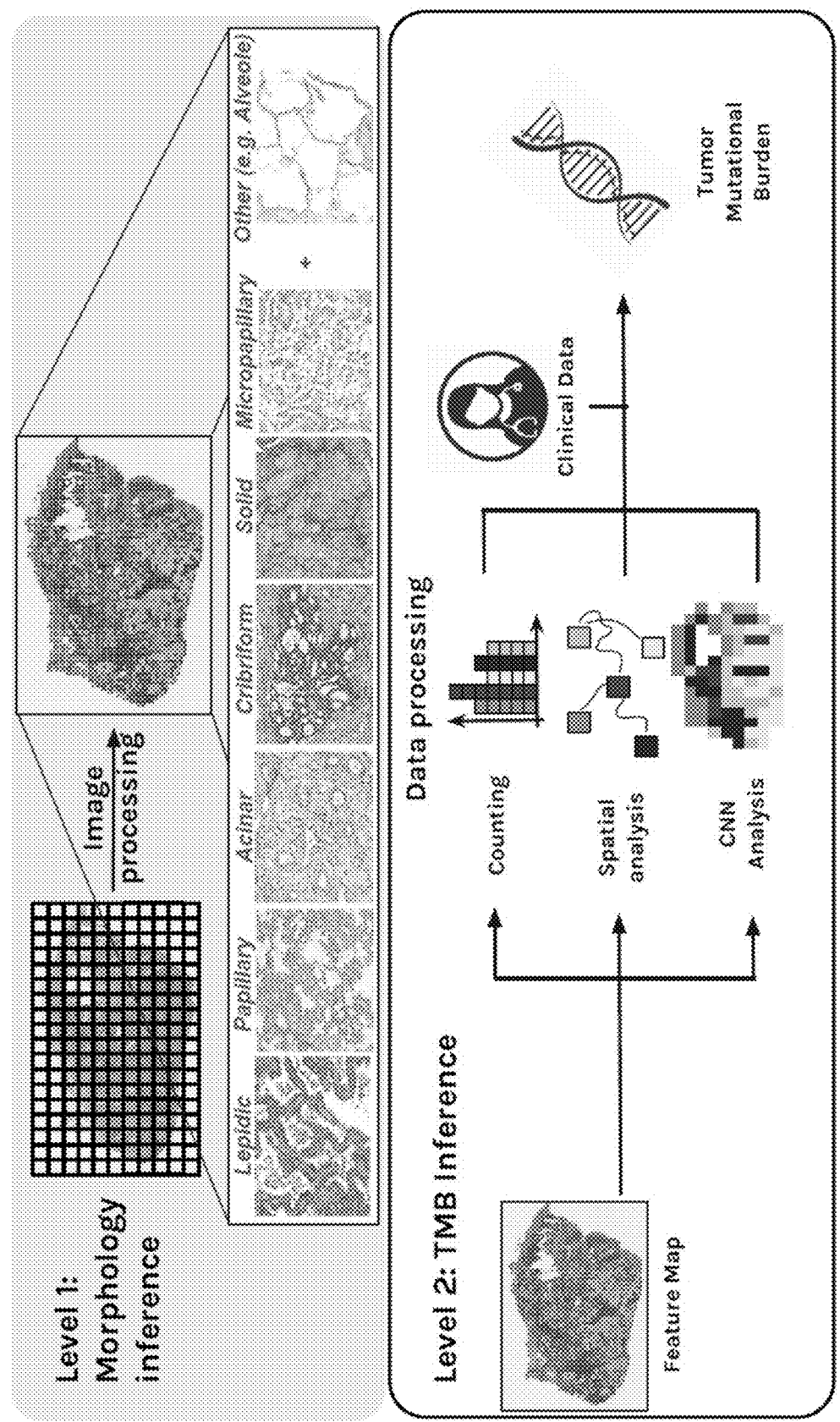
FIG. 3 illustrates a two-level image processing technique to infer a value of a biomarker according to aspects of the present invention.

FIG. 3 illustrates an image-processing system that infers a value of a biomarker (e.g., PD-L1 status, tumor mutational burden, or IFNγ gene expression signatures) according to aspects of the present invention. The image processing system 300 can utilize a two-level protocol to process images (e.g., of stained samples) to provide indications of one or more of biological features, structures, and/or structure classifications (e.g., necrosis, mitosis, anthracotic pigment, lymphocyte, macrophage, mild cellular atypia, moderate cellular atypia, severe cellular atypia, low nuclear grade, mid nuclear grade, high nuclear grade, a specific tumor architecture (e.g. lepidic, papillary, mucinous, acinar, cribriform, solid, micropapillary in adenopapillary lung cancer), endothelial vasculature, tumor associated fibroblasts, stromal fibroblasts, debris, artefacts including folds and tears, overall non-tumor structures, etc.) shown in the image. Level 1 processing one or more image processing techniques that modify, translate, and/or transform the image to identify biological features. For instance, stain normalization, image segmentation (e.g. patching), edge detection, signal processing, segmentation, feature detection, and/or the like may be performed to provide an indication of biological features present in the image or portions thereof.

A feature map (e.g., in which each patch or the overall image is associated with one or more biological features) can be generated using the detected biological features. Edge detection may be used to identify edges in the image to detect structures shown in the image and/or each patch. In some instances, the image and/or a patch may be associated with one of lepidic, mucinous, papillary, mucinous, acinar, cribriform, solid, micropapillary, lobular carcinoma in-situ, infiltrating lobular, medullary, tubular, apocrine, solid/comedo, cribriform-comedo, comedonecrosis, clear cell, serrated, signet ring cell, basaloid, clear cell, budding tumor foci, or single cell invasion features. In other instances, in addition to one of the aforementioned biological features, the image and/or each patch may be associated with one or more of necrosis, mitosis, nuclear atypia, anthracotic pigment, lymphoctyte, macrophage, endothelial vasculature, tumor associated fibroblasts, stromal fibroblasts, debris, artefacts including folds and tears, overall non-tumor structures, and/or the like. The feature map can be a data structure that associates each patch with the one or more biological features detected therein. In some instances, the feature map may be rendered to display the biological features of each patch.

The feature map generated as part of Level 1 processing may be used as input at Level 2 processing. At Level 2 processing, the feature map may be processed using one or more statistical techniques (e.g., counting, density analysis, spatial analysis, a convolutional neural network analysis, etc.) to infer a value corresponding to a biomarker such as, but not limited to, PD-L1 status, tumor mutational burden, or IFNγ gene expression signatures. For example, the one or more statistical techniques may include determining number of patches corresponding to each biological feature, determining a percentage of each biological feature detected in the image, determining a statistical sampling, determining a density of each biological feature, determining a proximity each biological feature to other biological features, determining spatial analysis of each biological feature, using convolutional neural network analysis, and/or the like. In some instances, the results of the one or more statistical techniques (and/or a machine learning model) may provide an estimation of PD-L1 status, tumor mutational burden, or IFNγ gene expression signatures. The image, the data obtained processing the image, and the estimation of the biomarker can be stored and/or distributed to a pathologist, a patient from which the biological sample was sourced, the patient's doctor, and/or the like.

Figure 4:
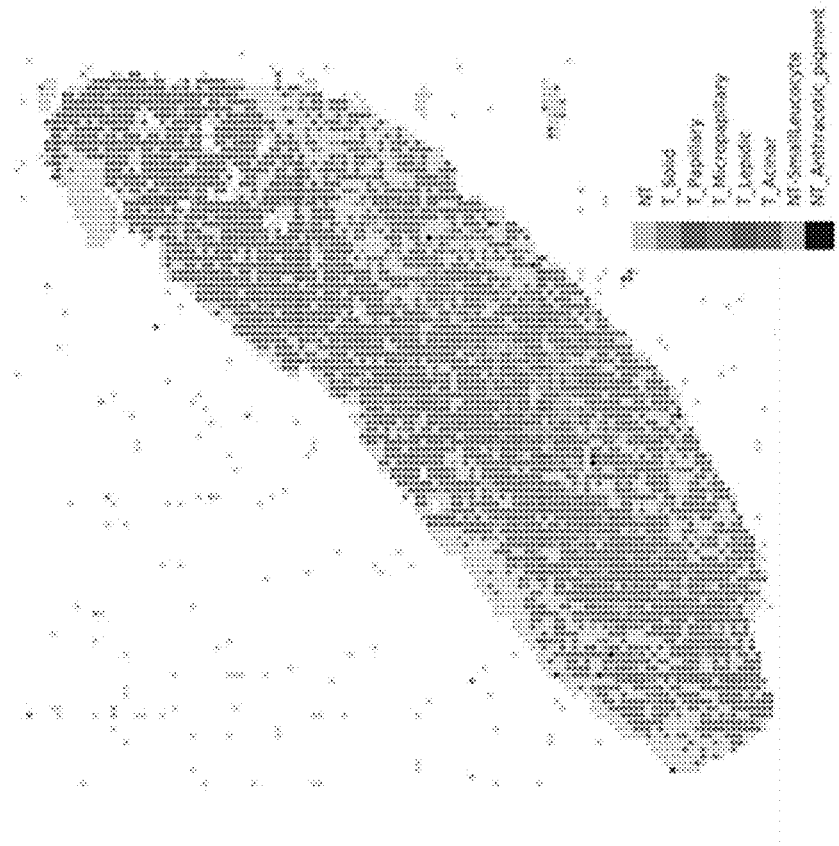
FIG. 4 illustrates exemplary intermediate output of an image processing system that identifies biological features present in an image of a H&E stained biopsy sample of a Stage IB tumor according to aspects of the present invention.
Figure 4:
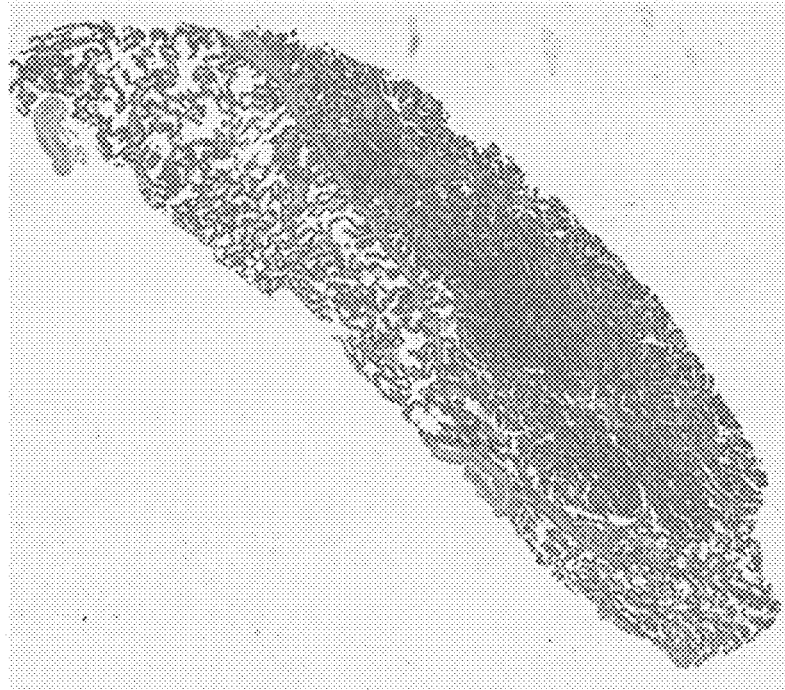

FIG. 4 illustrates exemplary intermediate output of an image processing system that identifies biological features present in an image of an H&E stained biopsy sample of a Stage IB tumor according to aspects of the present invention. On left is an input image of a Stage IB tumor (e.g., H&E stained biopsy sample) before image processing. On the right is a feature map generated as part of Level 1 processing (e.g., as described in FIG. 3 above). The feature map may represent at least one biological feature associated with each patch of a set of patches. For example, each patch can be tagged as depicting NT (e.g., non-tumor, including anthracotic pigment, small leucocyte features, normal tissue structures or image artifacts), a tumor structure (e.g. lepidic, papillary, mucinous, acinar, cribriform, solid, micropapillary in adenocarcinoma lung cancer), or a nuclear feature (e.g. nuclear atypia or mitotic figures).

For example, a spatial analysis right hand image of FIG. 4 indicates the presence of large, contiguous (high density) patches associated with acinar adjacent to large, contiguous patches associated with papillary. The absence of significant biological features such as solid and micropapillary (e.g., in terms of patch count or density), indicates a less advanced form of the disease and an inference of a relative low value of the tumor mutational burden.

Figure 5:
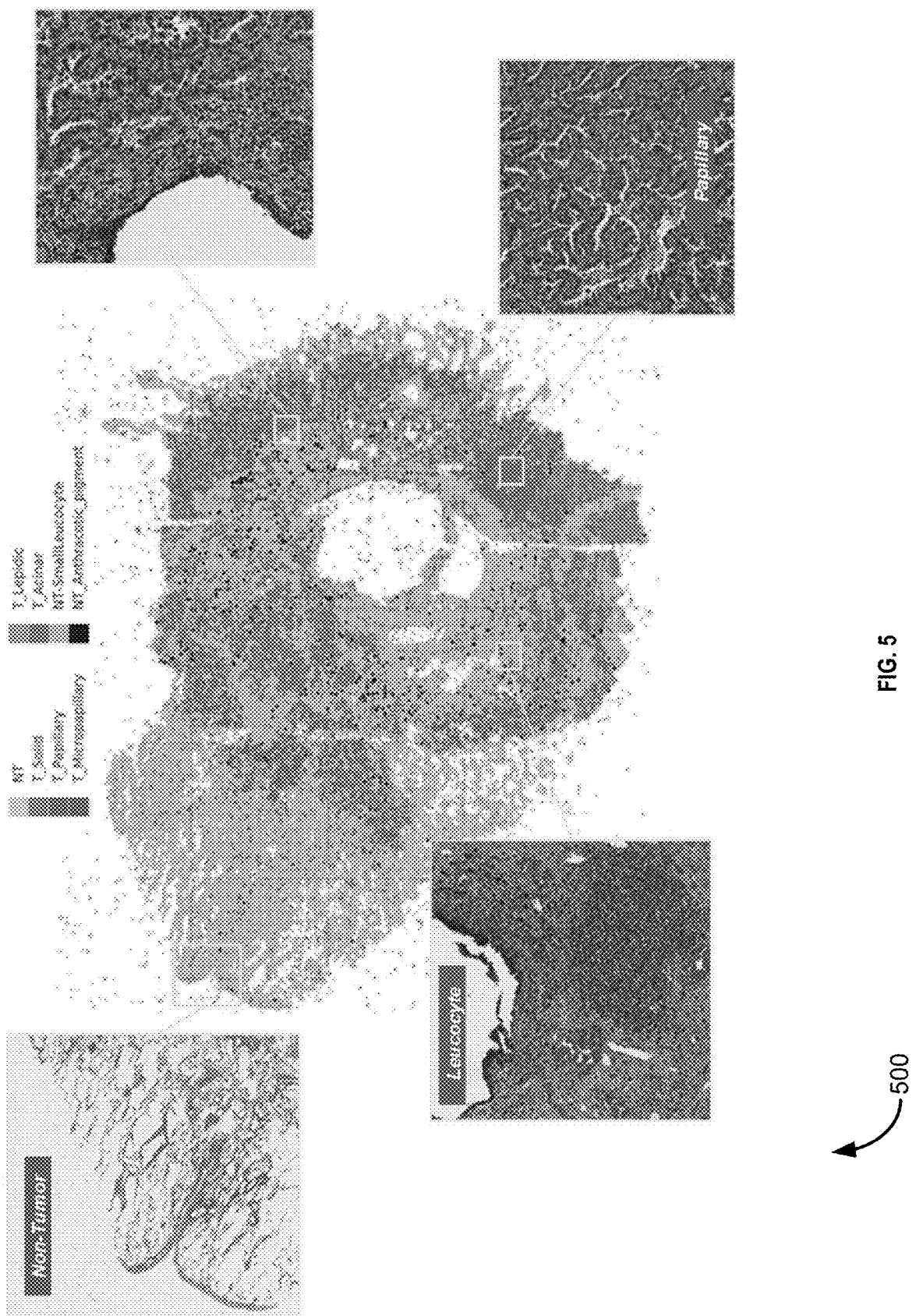
FIG. 5 illustrates exemplary intermediate output of an image processing system that identifies features present in an image of a H&E stained biopsy sample of a Stage IV tumor according to aspects of the present invention.

FIG. 5 illustrates exemplary intermediate output of an image processing system that identifies biological features present in an image of a H&E stained biopsy sample of a Stage IV tumor according to aspects of the present invention. The feature map 400 provides an indication of at least one biological feature associated with each patch of a set of patches. Each patch is associated with NT (e.g., non-tumor, including anthracotic pigment, or small leucocyte features, normal tissue structures or image artifacts), a tumor structure (e.g. lepidic, papillary, mucinous, acinar, cribriform, solid, micropapillary in adenocarcinoma lung cancer) or a nuclear feature (e.g nuclear atypia or mitotic figures). In contrast to FIG. 4, the feature map 500 is representative of a more advanced form of disease.

For example, a spatial analysis of the feature map 500 indicates the presence of large, contiguous (high density) patches associated with solid architecture and sparse patches associated with micropapillary architecture. Although there are still significant patches associated with both papillary and acinar architecture, the increased presence of advanced stage biological features throughout the image (rather than isolated within a small section) indicates a more advanced form of disease and an inference of a higher value of the tumor mutational burden than the feature map 400 of FIG. 4.

Figure 6:
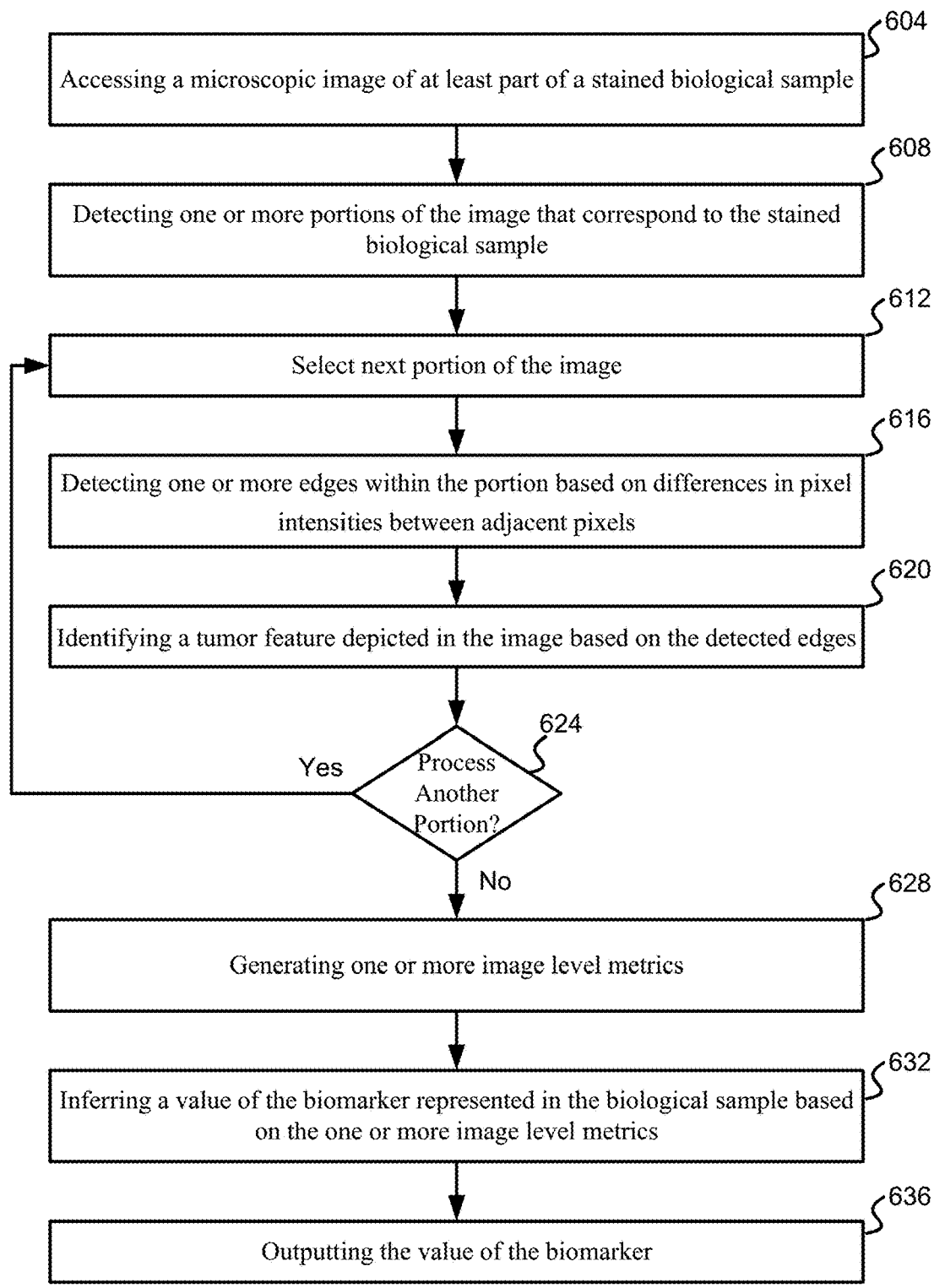
FIG. 6 illustrates exemplary flowchart illustrating an processing images of stained biological samples to infer PD-L1 status, tumor mutational burden, or IFNγ gene expression signatures according to aspects of the present invention.

FIG. 6 illustrates exemplary flowchart illustrating an image processing process 600 of an image of a stained biopsy sample to infer PD-L1 status, tumor mutational burden, or IFNγ gene expression signatures according to aspects of the present invention. At block 604, a microscopic image of at least part of a stained biological sample is accessed. In some instances, the stained biological sample originates from normal tissue, cancerous tissue such as, but not limited to, non-small cell lung cancer (e.g., squamous cell carcinoma, adenocarcinoma, and large cell carcinoma, etc.)., melanoma (e.g., superficial spreading, nodular, lentigo melanoma, acral lentiginous, etc.) or any other type of malignant or abnormal human tissue. The microscopic image can be a high resolution image (e.g., greater than a gigapixel) or any resolution with sufficient detail to enable image processing.

At block 608, one or more portions of the image that correspond to the stained biological sample can be detected. The microscopic image may be pre-processed which can include segmentation (e.g., dividing the image into a set of overlapping or non-overlapping patches). Each patch may be analyzed to determine if the patch corresponds to the biological sample or not. For example, a portion of the microscopic image may correspond with the slide prepared with the stained biological sample. The one or more patches that do not correspond to the biological sample may be preemptively removed from the microscopic image to reduce the area of the image that will be processed. One or more of object recognition, pattern analysis, machine-learning, such as the machine-learning model described above, a pathologist, and/or the like may be used to identify the biological sample from portions of the image not including the biological sample. Pre-processing may also include stain normalization (e.g., to normalize images of biological samples stained with different stains or staining techniques), blurring and/or sharpening of one or more patches, etc.).

At block 612, a first patch of the set of patches is selected for processing (in steps 612-620) to identify one or more biological features that is represented by the portion of the microscopic image depicted within the patch. For adenocarcinoma lung cancers, the one or more biological features include signet ring cell, lepidic, mucinous, acinar, cribriform, solid, micropapillary, one or more tumor morphologies, endothelial vasculature, tumor associated fibroblasts, stromal fibroblasts, necrosis, nuclear grading/atypia, mitosis, anthracotic pigment, debris, artefacts, immune cells, and/or non-tumor structures. For melanomas, the one or more biological features may include one or more of endothelial vasculature, tumor associated fibroblasts, stromal fibroblasts, immune cells, necrosis, mitosis, debris, artefacts, and/or non-tumor structures. For breast cancer, the one or more features may include lobular carcinoma in-situ, infiltrating lobular, papillary, medullary, mucinous, tubular, apocrine, solid/comedo, cribriform-comedo, comedonecrosis, micropapillary, one or more tumor morphologies, endothelial vasculature, tumor associated fibroblasts, stromal fibroblasts, necrosis, nuclear grading/atypia, mitosis, debris, artefacts, immune cells, microcalcification and/or non-tumor structures. For colon cancer, the features may include cribriform-comedo, medullary, micropapillary, mucinous, serrated, signet ring cell, one or more tumor morphologies, endothelial vasculature, tumor associated fibroblasts, stromal fibroblasts, necrosis, nuclear grading/atypia, mitosis, anthracotic pigment, debris, artefacts, immune cells, microcalcification and/or non-tumor structures.

At block 616, each patch of the set of patches can be analyzed to detect variations in pixel intensity across adjacent pixels of the patch. Variations in pixel intensity may provide an indication of an edge. In some instances, edge detection may generate a transformed version of the image by removing (or suppressing) all pixels that do not correspond to a detected edge. Edge detection may include one or more image processing techniques as described above in connection with FIG. 1. One or more other image processing techniques may be performed before, during, or after edge detection to improve image processing of the patch. For example, the patch may be processed using a kernel to improve edge detection (e.g., by blurring, sharpening, an affine transformation, filtering, etc.).

At block 620, one or more biological features may be identified as being shown in the patch using the detected edges. One or more classification techniques may be performed to identify the one or more biological features. For example, one or more of object recognition, pattern analysis, a convolutional neural network, segmentation, a machine-learning model, a pathologist, and/or the like can be used to determine the biological feature(s). In some instances, each patch can be tagged with the one or more biological features detected as being shown by the patch.

At block 624, it is determined whether there are more patches that have yet to be processed. If there are additional patches to process then control shifts back to block 612 where a next patch is selected for processing. In some instances, only a portion of the set of patches need be processed. For example, particular contiguous regions of the image (selected by a user, a pathologist, a machine-learning model, a pre-processing step performed during block 608, information obtained and/or learned from an image processing performed on a set of previous images, and/or the like) may be processed to identify the one or more biological features represented therein while the remaining portions of the image may be ignored. The remaining portions of the image may not contribute to inferring the tumor mutational burden, PD-L1 status, or levels of the interferon gamma gene expression signature (e.g., due to representing non-tumor tissue, the slide prepared to image the biological sample, or redundant, etc.). If there are no further patches to process or if it is determined that all patches of the set of patches that should be process, have been processed, then the process continues to block 628.

At block 628, the one or more image level metrics may be generated using the biological features identified for the portions of the image. The image level metrics may extrapolate the one or more biological features of each portion of the image to identify characteristics of the image as a whole. For example, higher densities of one particular biological feature (e.g., solid) over another particular biological feature (e.g., lepidic) can indicate that the tumor from which the biological sample originated is more advanced. The image level metrics may include spatial relationships among biological features, percentage of each biological feature detected in the set of patches, statistical sampling, density of each detected biological feature, proximity of a biological feature to another biological feature, spatial orientation of a biological feature, applying a kernel to identify biological feature topologies, counting parameters, a applying a convolutional neural network, a linear or non-linear regressions and/or like. In some instances, the one or more image level metrics can include a feature map that represents the patches with an identifier unique to the one or more biological features tagged by the patch. The feature map may be rendered (e.g., as depicted in FIGS. 4 and 5) in which the identifier of each patch may be represented as a color or other visual identifier (e.g., shading, lines such as cross-hatching, columns, stripes, etc., a symbol, graphical image, animation, and/or the like).

At block 632, one or more values corresponding to the selected one or more biomarkers is inferred using the one or more image level metrics. For example, if the one or more image level metrics indicate a larger amount of micropapillary biological features, it may indicate a higher tumor mutational burden than an absence of micropapillary biological features. In some instances, the one or more image level metrics (or biological features) may be weighted based on a particular biomarker of interest. For example, parameters corresponding to solid and micropapillary features may be weighted higher in determining a value for the tumor mutational burden than for IFNγ gene expression signatures. On the other hand, parameters corresponding to small leukocyte tumor infiltrations may be weighted higher in determining a value for IFNγ gene expression signatures. Similarly, parameters corresponding to small leukocyte tumor infiltrations would have a higher weight for determining a value for PD-L1 status (e.g., based on PD-L1 status being correlated with IFNγ gene signature expression). While exemplary relative weights have been described in connection with determining values for tumor mutational burden, PD-L1 status, and IFNγ gene signature expression, features may be weighted higher, lower, or not weighted at all based on a selected biomarker, output from a machine-learning model, previous image processing results, user input, and/or the like. For example, weights may vary (slightly or significantly) or stay the same from one image processing process to the next image processing process.

At block 636, the one or more values of the biomarker are output. Outputting a value may include presenting the value to a user, displaying the value, transmitting the value to one or more remote devices, storing the value in a database in connection with the image (and/or a patient record associated the biological sample), using the value as input into a machine-learning model, modifying one or more parameters/properties associated with processing subsequent images, and/or the like. After the one or more values are processed the process may determine if there are further images to process. If there are further images to process control may shift to 604 in which the new image is processed. If there are no more images to process, the process terminates. Although the blocks of FIG. 6 are described in a particular order, each block may be executed in any order and repeated any number of times during any performance of FIG. 6.

Various techniques and systems disclosed herein relate to inferring a tumor mutational burden based on processing of an image. It will be appreciated that, in some instances, similar or same techniques and/or systems may be used to additionally or alternatively infer one or more other biomarkers. For example, a biomarker can include a PD-L1 status or an interferon-gamma-related (IFN-γ-related) gene signature.

PD-L1 expression can represent or indicate a quantity of protein expression on tumor cells, immune cells, and other stromal cells within the tumor micro-environment. PD-L1 expression may be assessed using a wide variety of methods including, but not limited to, IHC assays (e.g. using the Dako 28-8, Dako 22c3, Ventana SP142 or Ventana SP263 assays).

The IFNγ gene expression signature can represent or indicate a quantity of mRNA expression evaluating two or more of the following loci: IFNγ, STAT1, CD274, CCR5, CD8A, CCL5, PTPRC, CCL5, TBX21, CXCL9, CXCL10, CXCL11, CXCL13, IDO1, PRF1, GZMA, CD74, CCR5, CD2, IL2RB, CD3D, CD4, CXCR6, CD27, PRF1, GZMB, LAG3 and MUCH HLA-DRA. Experimental techniques used to evaluate mRNA expression level include but are not limited to quantitative reverse transcriptase polymerase chain reaction (qRT-PCR), barcode-based methods (e.g. nanostring), mRNA in situ hybridization (ISH), array based methods, or mRNA sequencing.

In some instances, a multi-level approach is used to infer a biomarker status for a whole slide. A first processing can include dividing an input image into multiple patches and classifying each patch. The classification for each patch can indicate whether it is estimated that a given biological feature (e.g., tumor morphology and/or mitotic indicators) is present or absent Patch segmentation may be performed to segment out and hence more precisely localize a feature of interest, such as immune cells in a patch.

Figure 7:
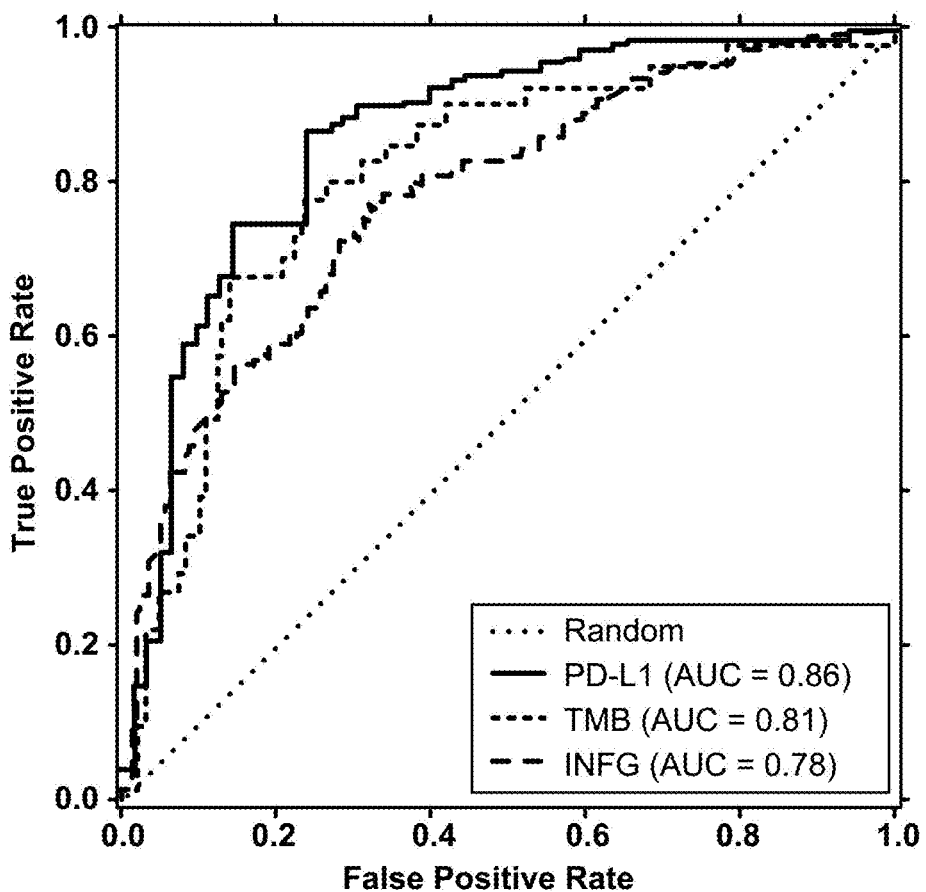
FIG. 7 illustrates results for processing images of stained lung adenocarcinoma samples to infer PD-L1 status, tumor mutational burden, or IFNγ gene expression signatures according to aspects of the present invention.

A second processing can include aggregating the classifications across patches and processing the aggregated classifications to generate a whole-slide biomarker status inference. For example, the processing of the aggregated classifications can include applying a linear regression or trained machine-learning model (e.g., random forest or neural network) to the classifications. A neural network may process the classifications by receiving, as input, the output image from the first-level model (e.g., a feature map). In addition to learning how whole-slide level outputs relate to, for example, feature proportions, the neural network can also learn spatial structures between different features. FIG. 7 illustrates results of inferring whole-slide presence of biomarkers that include PD-L1, TMB and INFG. The high areas under the curves indicate that the neural network successfully learned to classify whole-cell images. The neural network can include a convolutional network with convolutional layers that are rotation and flip invariant and that uses fewer trainable parameters than regular convolutions. Thus, model performance on smaller data sets can be improved.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

It is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure.

While the principles of the disclosure have been described above in connection with specific apparatuses and methods, it is to be clearly understood that this description is made only by way of example and not as limitation on the scope of the disclosure.

What is claimed is:

1. A method comprising:
    detecting one or more portions of an image that correspond to a biological sample, the image of at least a part of the biological sample;
    identifying, for each portion of the one or more portions of the image, a biological feature that is represented by the portion by:
        detecting one or more edges based on differences in pixel intensities between adjacent pixels; and
        identifying the biological feature based on the detected edges;
    generating one or more image level metrics based on the identified biological features;
    assigning, based on a first biomarker of interest, a weight to each identified biological feature;
    determining a value of a second biomarker represented in the biological sample based on the one or more image level metrics and the weights assigned to each identified biological feature; and
    outputting the value of the second biomarker.

2. The method of claim 1, wherein the first biomarker and the second biomarker are the same biomarker.

3. The method of claim 1, wherein the first or second biomarker is associated with cancer.

4. The method of claim 3, wherein the cancer includes lung cancer.

5. The method of claim 3, wherein the cancer includes a solid tumor.

6. The method of claim 1, wherein the first or second biomarker is one or more of tumor mutational burden (TMB), programmed death ligand-1 (PD-L1), or interferon gamma (IFNγ) gene signature.

7. The method of claim 1, wherein the biological feature includes a tumor architecture or nuclear morphology.

8. The method of claim 1, wherein the one or more image level metrics include a count of a feature, deriving spatial relationships within and between two or more biological features, and/or applying a kernel to identify feature topologies.

9. The method of claim 1, further comprising generating a prediction of a clinical outcome of a patient based on the value of the second biomarker.

10. The method of claim 1, further comprising:
  detecting a depiction of one or more immune cell sub-populations, wherein the immune cell sub-populations include one or more of small lymphocytes, macrophage, natural killer cells, neutrophils and/or eosinophils; and
  determining a quantity and/or a type associated with the one or more immune cell sub-populations, wherein determining the value of the biomarker is further based on the quantity and/or the type associated with one or more immune cell sub-populations.

11. The method of claim 1, further comprising detecting a nuclear structure of one or more cells depicted in a portion of the image of the one or more portions of the image, wherein determining the value of the biomarker is further based on the nuclear structure of the one or more cells depicted in the image.

12. A system comprising:
  a non-transitory computer-readable medium; and
  one or more processors communicatively coupled to the non-transitory computer-readable medium, the one or more processors configured to execute processor-executable instructions stored in the non-transitory computer-readable medium to:
    detect one or more portions of an image that correspond to a biological sample, the image of at least a part of the biological sample;
    identify, for each portion of the one or more portions of the image, a biological feature that is represented by the portion by:
      detecting one or more edges based on differences in pixel intensities between adjacent pixels; and
      identifying the biological feature based on the detected edges;
    generate one or more image level metrics based on the identified biological features;
    assign, based on a first biomarker of interest, a weight to each identified biological feature;
    determine a value of a second biomarker represented in the biological sample based on the one or more image level metrics and the weights assigned to each identified biological feature; and
    output the value of the second biomarker.

13. The system of claim 12, wherein the first biomarker and the second biomarker are the same biomarker.

14. The system of claim 12, wherein the first or second biomarker is associated with cancer or is one or more of a tumor mutational burden (TMB), programmed death ligand-1 (PD-L1), or interferon gamma (IFNγ) gene signature.

15. The system of claim 12, wherein the biological feature includes a tumor architecture or nuclear morphology.

16. The system of claim 12, wherein the one or more image level metrics include a count of a feature, deriving spatial relationships within and between two or more biological features, and/or applying a kernel to identify feature topologies.

17. The system of claim 12, wherein the one or more processors are configured to execute further processor-executable instructions stored in the non-transitory computer-readable medium to generate a prediction of a clinical outcome of a patient based on the value of the second biomarker.

18. The system of claim 12, wherein the one or more processors are configured to execute further processor-executable instructions stored in the non-transitory computer-readable medium to:
  detect a depiction of one or more immune cell sub-populations, wherein the immune cell sub-populations include one or more of small lymphocytes, macrophage, natural killer cells, neutrophils and/or eosinophils; and
  determine a quantity and/or a type associated with the one or more immune cell sub-populations, wherein determining the value of the biomarker is further based on the quantity and/or the type associated with one or more immune cell sub-populations.

19. The system of claim 12, wherein the one or more processors are configured to execute further processor-executable instructions stored in the non-transitory computer-readable medium to detect a nuclear structure of one or more cells depicted in a portion of the image of the one or more portions of the image, wherein determining the value of the biomarker is further based on the nuclear structure of the one or more cells depicted in the image.

20. A non-transitory computer-readable medium comprising processor-executable instructions configured to cause one or more processors to:
  detect one or more portions of an image that correspond to a biological sample, the image of at least a part of the biological sample;
  identify, for each portion of the one or more portions of the image, a biological feature that is represented by the portion by:
    detecting one or more edges based on differences in pixel intensities between adjacent pixels; and
    identifying the biological feature based on the detected edges;
  generate one or more image level metrics based on the identified biological features;
  assign, based on a first biomarker of interest, a weight to each identified biological feature;
  determine a value of a second biomarker represented in the biological sample based on the one or more image level metrics and the weights assigned to each identified biological feature; and
  output the value of the second biomarker.

* * * * *